United States Patent
Dropps et al.

(10) Patent No.: US 6,898,463 B2
(45) Date of Patent: May 24, 2005

(54) CURRENT MONITOR FOR AN IMPLANTABLE MEDICAL DEVICE

(75) Inventors: Frank R. Dropps, Maple Grove, MN (US); Dennis A. Brumwell, Bloomington, MN (US)

(73) Assignee: Medtronic, Inc., Minneapolis, MN (US)

( * ) Notice: Subject to any disclaimer, the term of this patent is extended or adjusted under 35 U.S.C. 154(b) by 478 days.

(21) Appl. No.: 10/102,076

(22) Filed: Mar. 19, 2002

(65) Prior Publication Data

US 2003/0181953 A1 Sep. 25, 2003

(51) Int. Cl.$^7$ ................................................ A61N 1/37
(52) U.S. Cl. ............................ 607/27; 607/34; 607/63
(58) Field of Search ............................. 607/27, 34, 63

(56) References Cited

U.S. PATENT DOCUMENTS

| | | | |
|---|---|---|---|
| 4,332,256 A | | 6/1982 | Brownlee et al. |
| 4,556,061 A | | 12/1985 | Barreras et al. |
| 5,137,020 A | * | 8/1992 | Wayne et al. ................. 607/29 |
| 5,163,428 A | * | 11/1992 | Pless ............................... 607/5 |
| 5,237,991 A | | 8/1993 | Baker, Jr. et al. |
| 5,372,605 A | * | 12/1994 | Adams et al. ................. 607/5 |
| 5,423,871 A | * | 6/1995 | Hoegnelid et al. ............ 607/28 |
| 5,847,551 A | | 12/1998 | Arora et al. |
| 6,241,751 B1 | * | 6/2001 | Morgan et al. ................ 607/8 |
| 6,549,807 B1 | * | 4/2003 | Kroll ............................ 607/34 |
| 6,553,263 B1 | * | 4/2003 | Meadows et al. ............. 607/61 |

FOREIGN PATENT DOCUMENTS

WO     WO 02/053223 A2     7/2002

* cited by examiner

*Primary Examiner*—Kennedy Schaetzle
(74) *Attorney, Agent, or Firm*—Girma Wolde-Michael; Paul H. McDowall

(57) ABSTRACT

A method and an apparatus for performing a device component failure analysis in an implantable medical device using current consumption data. A current consumption signal relating to current consumption in an implantable medical device is generated. The current consumption signal is then processed. A defect of a component in the implantable medical device is assessed in response to the processing of the current consumption signal and appropriate action is taken, such as selecting alternate therapies, generating an alert signal, and turning off circuits corresponding to the assessed defect.

28 Claims, 8 Drawing Sheets

CURRENT MONITOR FOR AN IMPLANTABLE MEDICAL DEVICE

FIELD OF THE INVENTION

This invention relates generally to acquisition of physiological data, and, more particularly, to a method and apparatus for monitoring current consumption in an implantable medical device for evaluating component performance.

DESCRIPTION OF THE RELATED ART

The technology explosion in the implantable medical device industry has resulted in many new and innovative devices and methods for analyzing and improving the health of a patient. The class of implantable medical devices now include pacemakers, implantable cardioverters, defibrillators, neural stimulators, and drug administering devices, among others. Today's state-of-the-art implantable medical devices are vastly more sophisticated and complex than earlier ones, capable of performing significantly more complex tasks. The therapeutic benefits of such implantable medical devices have been well proven.

There are many implementations of implantable medical devices that provide data acquisition of important physiological data from a human body. Many implantable medical devices are used for cardiac monitoring and therapy. Often these implantable medical devices comprise sensors that are placed in blood vessels and/or chambers of the heart. These implantable medical devices are often operatively coupled with implantable monitors and therapy delivery devices. For example, such cardiac systems include implantable heart monitors and therapy delivery devices, such as pacemakers, cardioverters, defibrillators, heart pumps, cardiomyostimulators, ischemia treatment devices, drug delivery devices, and other heart therapy devices. Most of these cardiac systems include electrodes for sensing and gain amplifiers for recording and/or driving sense event signals from the inter-cardiac or remote electrogram (EGM).

As the functional sophistication and complexity of implantable medical device systems have increased over the years, it has become increasingly useful to include efficient and varied forms of energy delivery systems in the implantable medical device. For example, today's implantable medical devices may deliver a number of types of cardiac therapy in a patient. Furthermore, cardiac therapy systems now provide for more rapid/frequent delivery of therapy. This tasks the energy delivery system within an implantable medical device even more.

One or more components in the implantable medical device may become defective, malfunction, or fail, which may cause unusual current consumption. Unusual current consumption in the implantable medical device may affect the overall power consumption of the implantable medical device, such that the life of the implantable medical device may be shortened. Additionally, delivery of therapy, e.g., charging up capacitor and policing the energy for a therapy delivery, may be comprised by excessive/unusual current consumption. Also, premature discharge of the battery device in the implantable medical device may occur. The life of the implantable medical device may be adversely affected by the malfunction(s) that my cause excessive/unusual power consumption.

The present invention is directed to overcoming, or at least reducing the effects of, one or more of the problems set forth above.

SUMMARY OF THE INVENTION

In one aspect of the present invention, a method is provided for performing a device component failure analysis in an implantable medical device using current consumption data. A current consumption signal relating to current consumption in an implantable medical device is generated. The current consumption signal is then processed. A defect of a component in the implantable medical device is assessed in response to the processing of the current consumption signal.

In another aspect of the present invention, a method of evaluating component performance in an implantable medical device includes generating a current consumption signal relating to current consumption in the implantable medical device, the generated current consumption signal including at least one of a current consumption signal relating to a quiescent current corresponding to the device, and a current consumption signal relating to an operating current corresponding to the device. A determination is made as to whether there is a current leak based upon the current consumption signal, and a component in the device is identified corresponding to the determined current leak.

In another aspect of the present invention, an implantable medical device includes a processor, and a control logic unit operatively coupled to the processor. The control logic unit generates at least one control signal in response to a command from the processor, and a memory unit, operatively coupled to the control logic unit, stores and provides data to the processor via the control logic unit. A power control unit is operatively coupled to the control logic unit and determines whether a component associated with the implantable medical device has malfunctioned.

BRIEF DESCRIPTION OF THE DRAWINGS

The inventions may be understood by reference to the following description taken in conjunction with the accompanying drawings, in which like reference numerals identify like elements, and in which.

Figure 1:
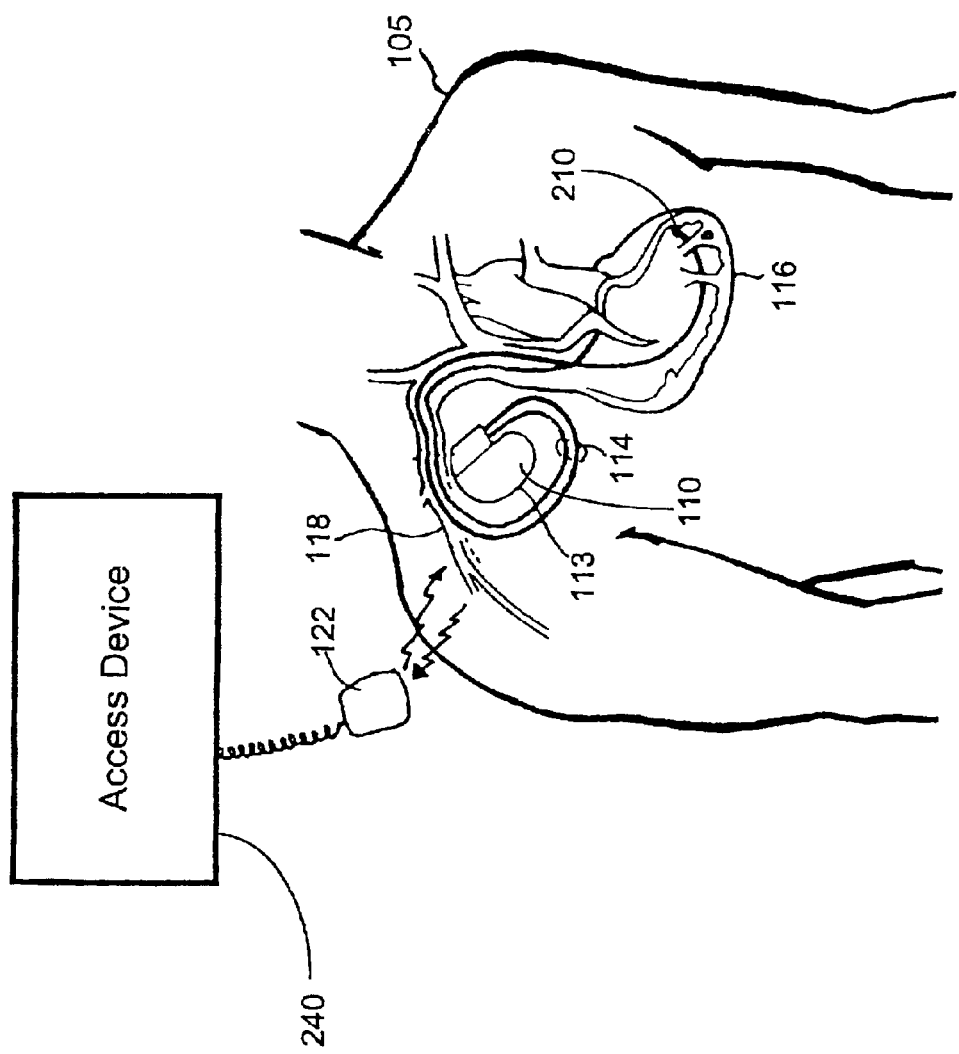
FIG. 1 is a simplified diagram of an implementation of an implantable medical device, in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

There are many discrete processes involving collecting, storing, and analyzing physiological data relating to a patient. Often, these tasks are performed by an implantable medical system, which includes an implantable medical device. Based upon the analysis performed by the implantable medical system, one or more therapies may be delivered to a particular portion of a patient's body. One example of such a therapy is a cardiac therapy, which is delivered to a patient's heart. The operation of an implantable medical device in the implantable medical system may be affected by malfunction of components (e.g., capacitors, inductors, resistors, transistors, crystal oscillators, etc.) in the implantable medical device.

Embodiments of the present invention provide for monitoring current consumption in an implantable medical device. Embodiments of the present invention provide for detecting component failures that may affect the power consumption, operation of the implantable medical device, and/or cause premature discharge of a battery in the implantable medical device. Implementing embodiments of the present invention can provide for predicting the lifetime of an implantable medical device that may have a leaky bypass or pacing capacitor. Embodiments of the present invention may be used to assess the condition of one or more electrical/electronic components in the implantable medical device.

Unusual current consumption, particularly quiescent current consumption, may be indicative of malfunction of a crystal oscillator that is used to drive digital circuitry in the implantable medical device. Utilizing the current monitoring functions provided by embodiments of the present invention, crystal oscillator behavior may be monitored such that any failure due to the loss of the hermetic seal in the implantable medical device may be detected. Furthermore, utilizing the present invention, malfunction of the crystal oscillator may be detected, reducing the possibility of crystal oscillator runaway behavior.

FIG. 1 illustrates one embodiment of implementing an implantable medical device into a human body. A sensor/therapy delivery device 210 (e.g., devices attached to leads 114) placed upon the heart 116 of the human body 105 is used to acquire and process physiological data. An implantable medical device 110 collects and processes a plurality of data acquired from the human body 105. In one embodiment, the implantable medical device 110 may be a pacemaker or a defibrillator. The data acquired by the implantable medical device 110 can be monitored by an external system, such as the access device 240 comprising a programming head 122, which remotely communicates with the implantable medical device 110. The programming head 122 is utilized in accordance with medical device programming systems known to those skilled in the art having the benefit of the present disclosure for facilitating two-way communication between the implantable medical device 110 and the access device 240.

In one embodiment, a plurality of access devices 240 can be employed to collect a plurality of data processed by the implantable medical device 110 in accordance with embodiments of the present invention. The implantable medical device 110 is housed within a hermetically sealed, biologically inert outer canister or housing 113, which may itself be conductive so as to serve as an electrode in the implantable medical device's 110 pacing/sensing circuit. One or more implantable medical device 110 sensors/leads, collectively identified with reference numeral 114 in FIG. 1 are electrically coupled to the implantable medical device 110 and extend into the patient's heart 116 via a vein 118. Disposed generally near a distal end of the leads 114 are one or more exposed conductive electrodes (sensors 210) for receiving electrical cardiac signals or delivering electrical pacing stimuli to the heart 116. The leads 114 may be implanted with their distal end situated in either the atrium or ventricle of the heart 116. In an alternative embodiment, the sensors 210, or the leads 114 associated with the sensors 210, may be situated in a blood vessel on the heart 116, such as a vein 118.

Figure 2:
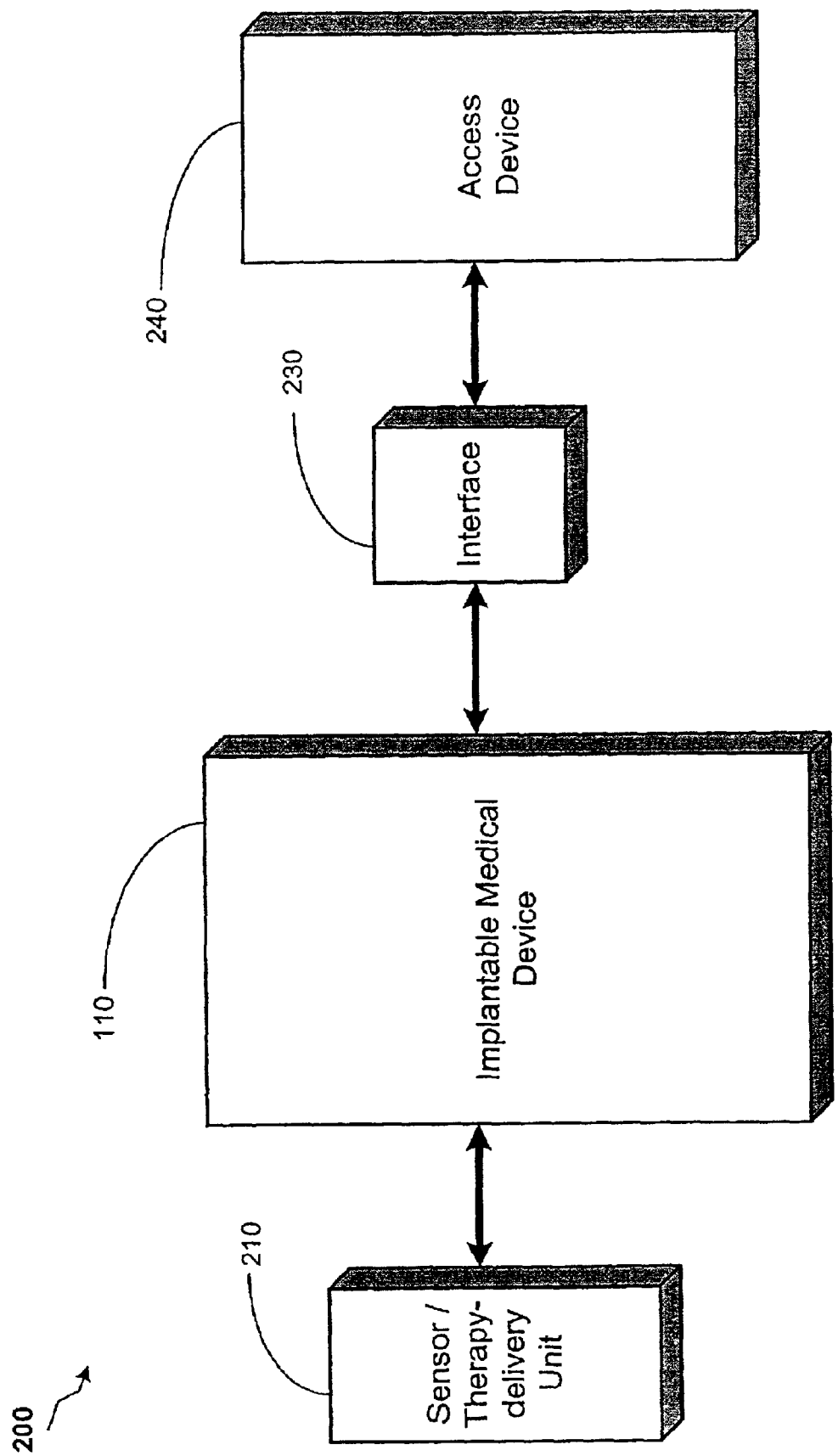
FIG. 2 illustrates a simplified block diagram representation of an implantable medical device system in accordance with one illustrative embodiment of the present invention.

Turning now to FIG. 2, a system 200, in accordance with one embodiment of the present invention, is illustrated. The system 200 comprises a sensor/therapy delivery device 210, an implantable medical device 110, an access device 240, and an interface 230 that provides a communication link between the implantable medical device 110 and the access device 240. Embodiments of the present invention provide a plurality of physiological data from the sensor 210, which are then processed and stored in the implantable medical device 110. Based upon physiological data and other factors, the implantable medical device 110 may deliver a therapy to a portion of the patient's body 105, such as the heart 116, via the sensor/therapy delivery device 210. The access device 240 can then be used to monitor and analyze the organized data from the implantable medical device 110 via the interface 230 and view results from delivered therapy. The access device 240 can be used to monitor the efficiency of the therapy delivered by the implantable medical device 110. The access device 240 can be used to detect, based upon data stored by the implantable medical device 110, to determine whether a therapy delivered was of proper energy intensity.

Figure 3:
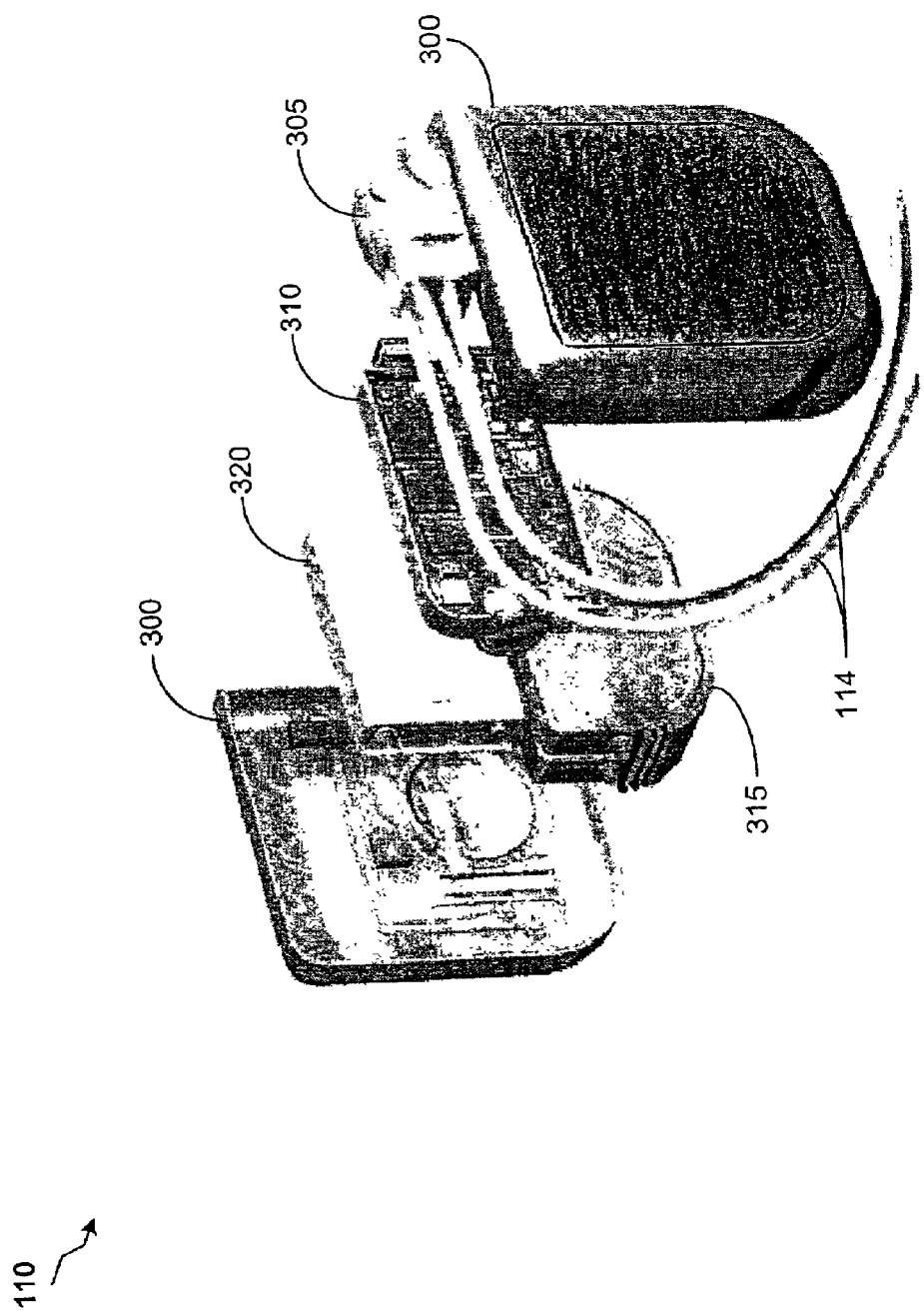
FIG. 3 illustrates an exploded view of an implantable medical device in accordance with one embodiment of the present invention.

Turning now to FIG. 3, a stylized three-dimensional depiction of the implantable medical device 110 in accordance with one embodiment of the present invention is illustrated. In one embodiment, a casing 300 may include a variety of elements including, but not limited to, a connector 305, a processor unit 310, a capacitor package 315, and a power source 320, such as a battery. The elements in the casing 300 may be positioned in any of a variety of locations. The capacitor package 315 and the battery 320 and electrically coupled to the processor unit 310. The leads 114 interface with the implantable medical device 110 through the connector 305 and electrically connect portions of the patient 105 such as the heart 116 to the implantable medical device 110.

The processor unit 310 detects and/or records electric cardiac signals that travel from the heart 116 along the leads 114 and enter the implantable medical device 110 through the connector 305. In one embodiment, the processor unit 310 uses the electric cardiac signals to determine when a cardiac event, such as a slow or erratic heart rate, occurs. In response to such a cardiac event or other conditions, the processor unit 310 administers one or a plurality of therapies. In one embodiment, a therapy delivered by the implantable medical devices 110 may be an electric pacing stimuli delivered to the heart 116. The implantable medical devices 110 may deliver the therapy by releasing energy stored in the capacitor package 315 and directing the energy through the connector 305 and onto the leads 114 to the heart 116. The capacitor package 315 may comprise one or more capacitors (not shown) that may store sufficient charge, such that when the charge is released, it can provide a cardiac therapy.

The battery 320 provides energy that is used to power the processor unit 310 and to recharge the capacitor package 315 between deliveries of therapy. In some cases, due to one or more electrical phenomenon, such as dipole polarization and current leakage, the capacitor package 315 may not charge up to, or retain, a desired charge level. Embodiments of the present invention provide for reducing the effect(s) of factors that compromise the energy levels of the charge held by the capacitor package 315. The system provided by embodiments of the present invention may be implemented into a variety of implantable medical devices 110 like heart pacemakers and drug delivery devices, for example.

Figure 4:
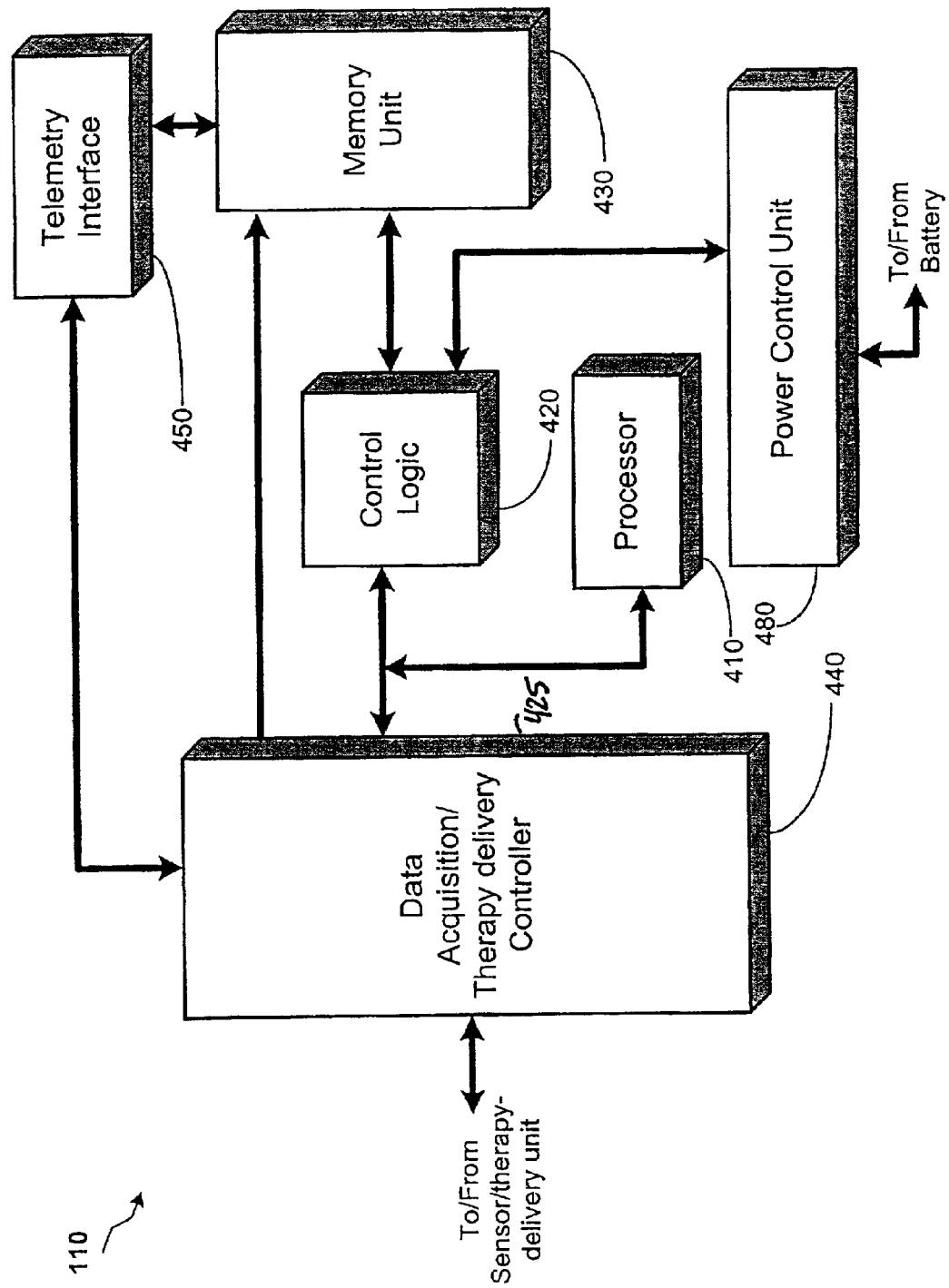
FIG. 4 illustrates a more detailed functional block diagram representation of the implantable medical device of FIGS. 1 and 2, in accordance with one illustrative embodiment of the present invention.

Turning now to FIG. 4, a more detailed block diagram depiction of one embodiment of the implantable medical device 110 is illustrated. In one embodiment, the block diagram shown in FIG. 4 provides a functional illustration of the processor unit 310 of FIG. 3. The implantable medical device 110 comprises a processor 410, a control logic unit 420, a memory unit 430, a data acquisition controller 440, a telemetry interface 450, and a power control unit 480. In one embodiment, a plurality of the blocks illustrated in FIG. 4 may be integrated as a single unit.

The processor 410 controls the operation of the implantable medical device 110. The processor 410 utilizes the control logic unit 420 to perform a plurality of operations, including memory access and storage operations. The processor 410 communicates with the control logic unit 420 and the data acquisition controller 440 via a bus line 425. The control logic unit 420 sends control signals to the memory unit 430 for controlling and installing memory, and to the data acquisition controller 440, which controls the acquisition of physiological data, delivery of therapy, and drives output signals to the telemetry interface 450. The data acquisition controller 440 can also be used to digitize the current consumption signal.

The telemetry interface 450 can facilitate real-time access of physiological data acquired by the data acquisition controller 440. Therefore, a physician can view physiological data on a real time basis by accessing the data acquisition controller 440, via the telemetry interface 450. The data acquisition controller 440 can prompt the implantable medical device 110 to acquire physiological data and/or deliver a cardiac therapy.

The implantable medical device 110 utilizes the power control unit 480, which may be coupled to the power source 320, to deliver a therapy (e.g., a cardiac therapy) to the patient 105. In one embodiment, the processor 410 controls the operations of the power control unit 480 via the control logic unit 420. The processor 410 monitors physiological data received by the data acquisition controller 440 and reacts accordingly. For example, when the processor 410 detects a cardiac event (e.g., rapid beating of the heart, fibrillation, etc.), the processor 410 may invoke a therapeutic response. The processor 410 then prompts the control logic unit 420 to invoke the power control unit 480. In response, the power control unit 480 may cause the power source 320 to send an appropriate amount of charge, which may be pre-programmed, to the capacitor package 315. As described above, the charge in the capacitor package 315 may be compromised due to losses caused by leakage current and/or dielectric polarization, among other factors.

The power control unit 480 is also capable of performing a current monitor function and storing data relating to the monitoring of the current consumption in the implantable medical device 110. The power control unit 480 is capable of monitoring the current consumption during normal operation of the implantable medical device 110, during accelerated operation of the implantable medical device 110 (e.g., during delivery of therapy), and/or during the period of time when the implantable medical device 110 is in a quiescent state (i.e., the quiescent current is monitored). In response to monitoring the current consumption of an implantable medical device 110, including the quiescent current consumption, assessment of the condition of one or more components in the implantable medical device 110 may be made. For example, malfunction and/or failures of components such as transistors, capacitors, crystal oscillators, etc. in the implantable medical device 110 may be made based upon the current consumption, in particular, based upon the quiescent current consumption.

Figure 5:
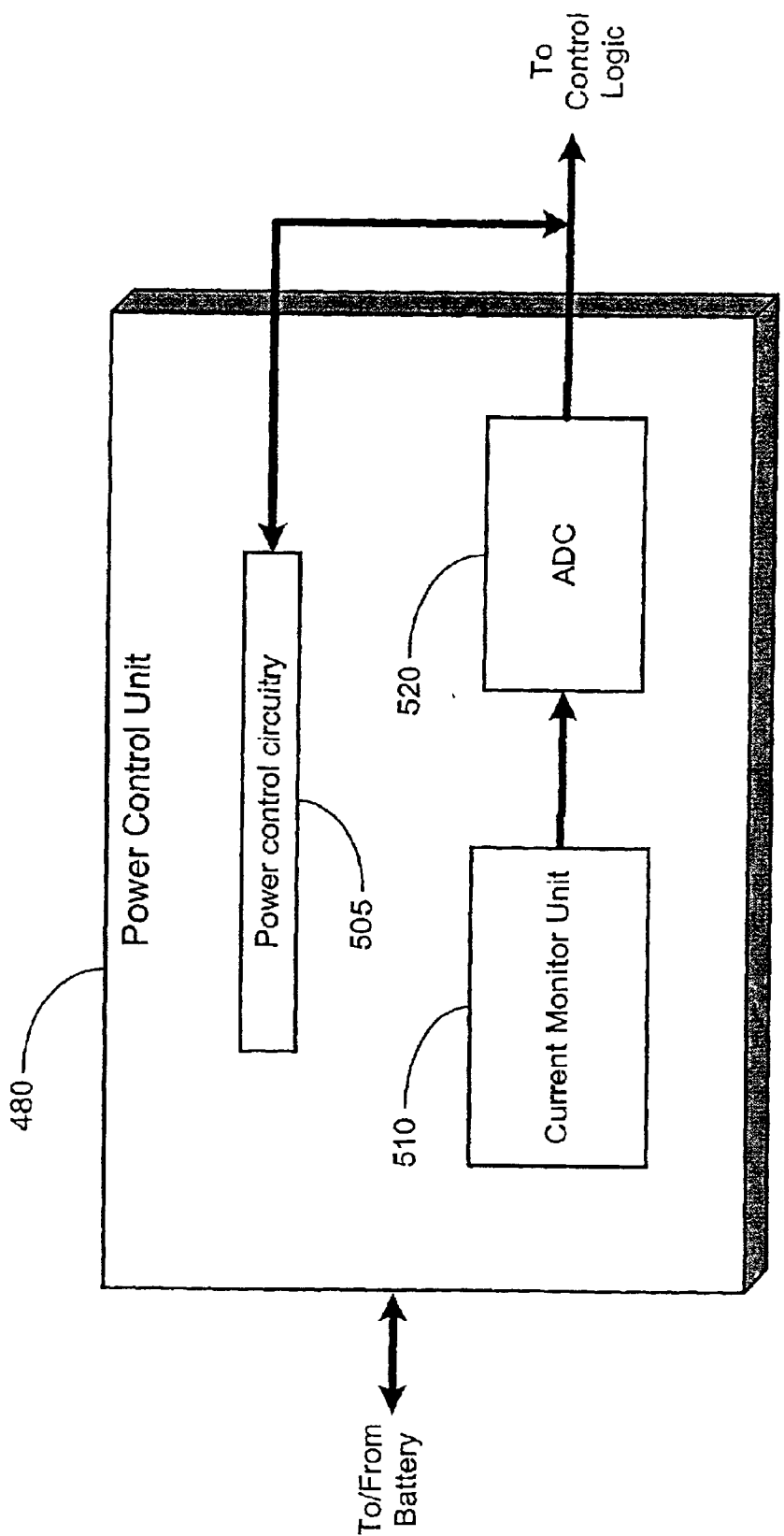
FIG. 5 illustrates a more detailed block diagram representation of the power control unit described in FIG. 4 in accordance with one illustrative embodiment of the present invention.

Turning now to FIG. 5, a more detailed block diagram depiction of one embodiment of the power control unit 480 is illustrated. In one embodiment, the power control unit 480 comprises a power control circuitry 505, a current monitor unit 510, and an analog-to-digital converter (ADC) 520. The operations performed by the power control circuitry 505 includes the power control functions described above. The current monitor unit 510 is capable of monitoring current consumed by the implantable medical device 110, due to its operation and/or the quiescent current consumption in the implantable medical device 110. The data acquisition controller 440 can also be used in place ADC 520 to digitize the current consumption signal.

The current monitor unit 510 acquires current consumption information and generates a current consumption analog signal. In one embodiment, the power control unit 480 converts the current consumption analog signal into a digital signal using the ADC 520. The digitized current consumption signal from the ADC 520 may then be sent to the control logic unit 420 for either transmission and/or storage in the memory unit 430. In one embodiment, the access device 240 may acquire and process the current consumption signal from the memory unit 430 for analysis. In an alternative embodiment, the processor 410 in the implantable medical device 110 may analyze the current consumption signal in order to determine whether any components in the implantable medical device 110 may be malfunctioning. It should be appreciated that the various functional blocks illustrated in FIGS. 4 and 5 may be partitioned and/or organized in a variety of manners and stay within the scope and spirit of the present invention. For example, in an alternative embodiment, much of the power control unit 480 may be implemented into the control logic unit 420.

Figure 6:
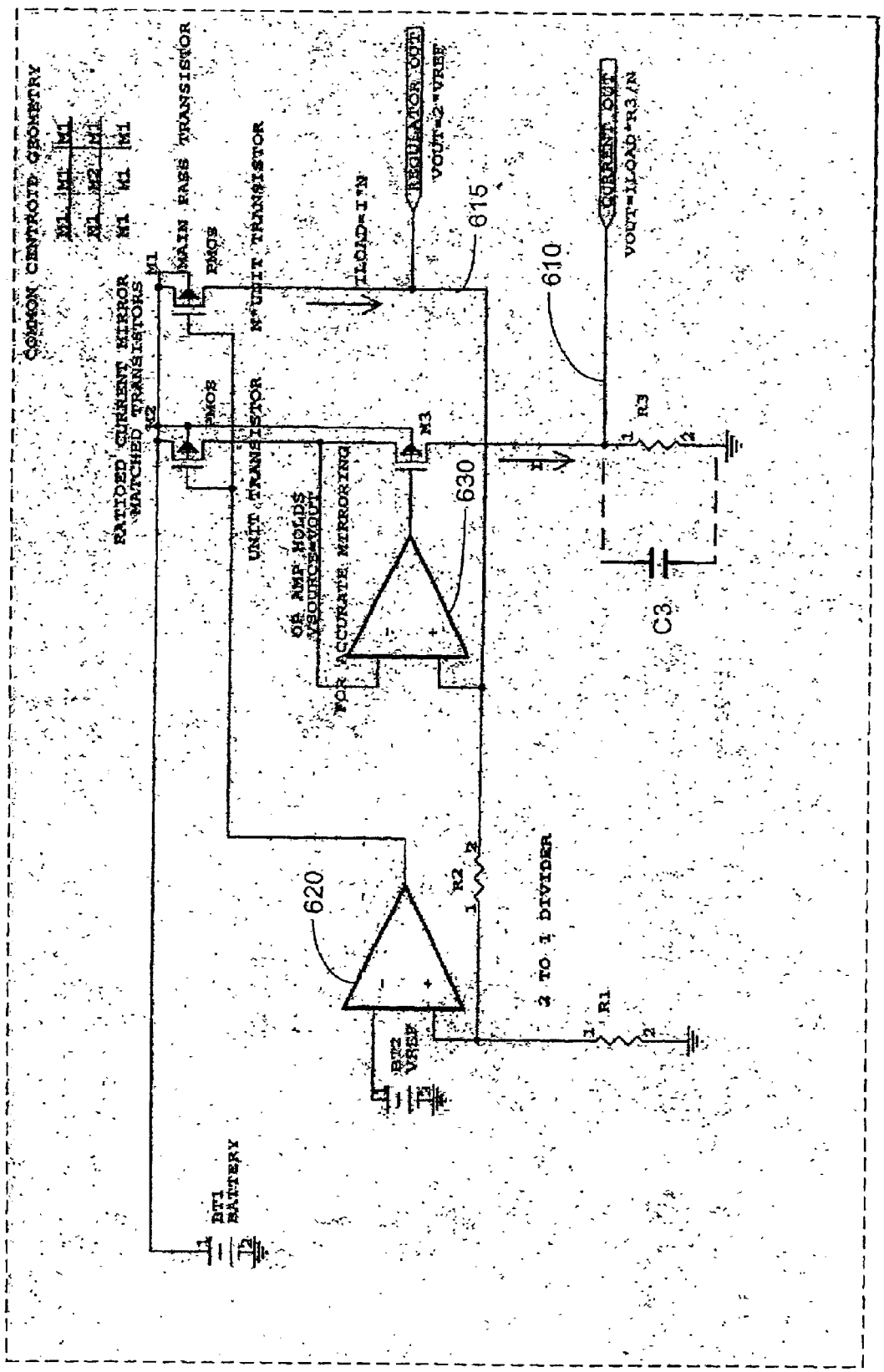
FIG. 6 illustrates a circuit diagram representation of a current monitor circuitry associated with the current monitor unit described in FIG. 5, in accordance with one illustrative embodiment of the present invention.

Turning now to FIG. 6, one embodiment of a current monitor circuit that may be implemented into the current monitor unit 510 is illustrated. As illustrated in FIG. 6, a pair of ratioed current mirror matched transistors M1, M2 and operational amplifiers (op amps) 620, 630 are provided to monitor the current consumed by the implantable medical device 110. Based upon the voltage level of a first battery BT1, whose signal is passed through the transistor M1 in response to the voltage level of a second battery BT2, the op amp 630 turns on a third transistor M3, which enables a signal on a line 610 that provides a current signal that is indicative of the current consumption by the implantable medical device 110.

In an alternative embodiment, the resistor R3 may be replaced by a capacitor C3 that may provide an integration function on the current signal on the line 610. When the integration of the current value is divided by the time of a sample period, an average current consumption value may be calculated. Therefore, an indication of the average current consumption by the implantable medical device 110 over a period of predetermined time can be generated. The current signal on the line 610 is then digitized by the ADC 520 for storage and/or transmission.

Figure 7:
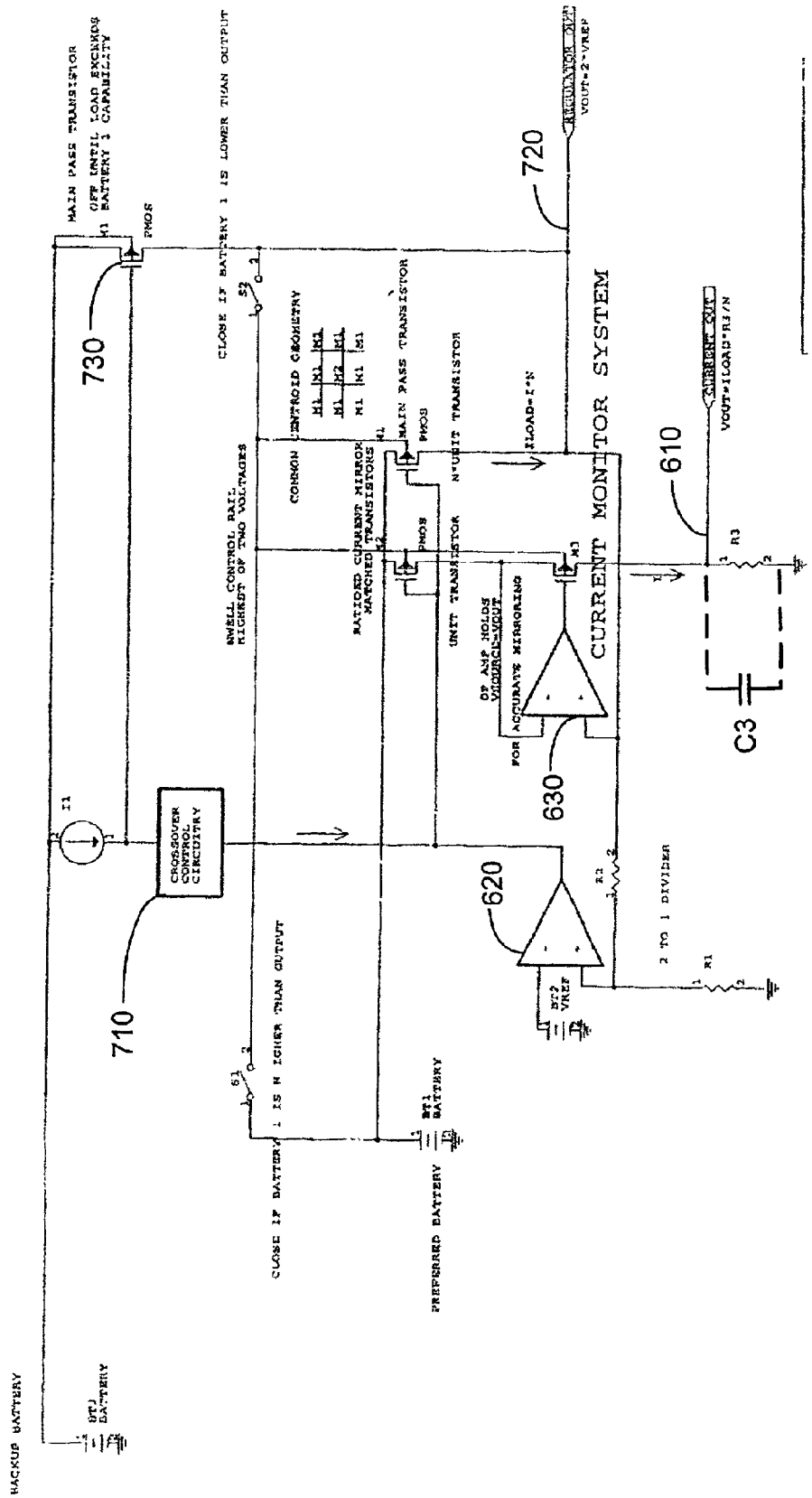
FIG. 7 illustrates a circuit diagram representation of an implementation of the current monitor circuitry described in FIG. 5, in accordance with one illustrative embodiment of the present invention.

Turning now to FIG. 7, one embodiment of implementing the current monitor circuit of FIG. 6 into a dual battery regulator with anti-reverse, is illustrated. Using the current monitor circuit 510, power from a plurality of batteries (e.g., the battery BT1 and a battery BT3) may be utilized based upon the power consumption and the battery level. A cross over control circuitry 710 in conjunction with switches S1, S2 may be used to regulate a power output from a plurality of batteries (e.g., from either battery BT1 or battery BT3). The circuit provides a regulated voltage signal on a line 720, using the battery BT1, for operation of the implantable medical device 110. When the load supported by the circuit of FIG. 7 exceeds the capabilities of the battery BT1, a main pass transistor 730 is turned on, the switch S1 is opened, and the switch S2 is closed, thereby providing power from battery BT3. The circuit illustrated in FIG. 7 provides a regulated voltage output on a line 720. The circuit of FIG. 7 also provides a current signal that is indicative of the current consumption by the implantable medical device 110, on the line 610.

Figure 8:
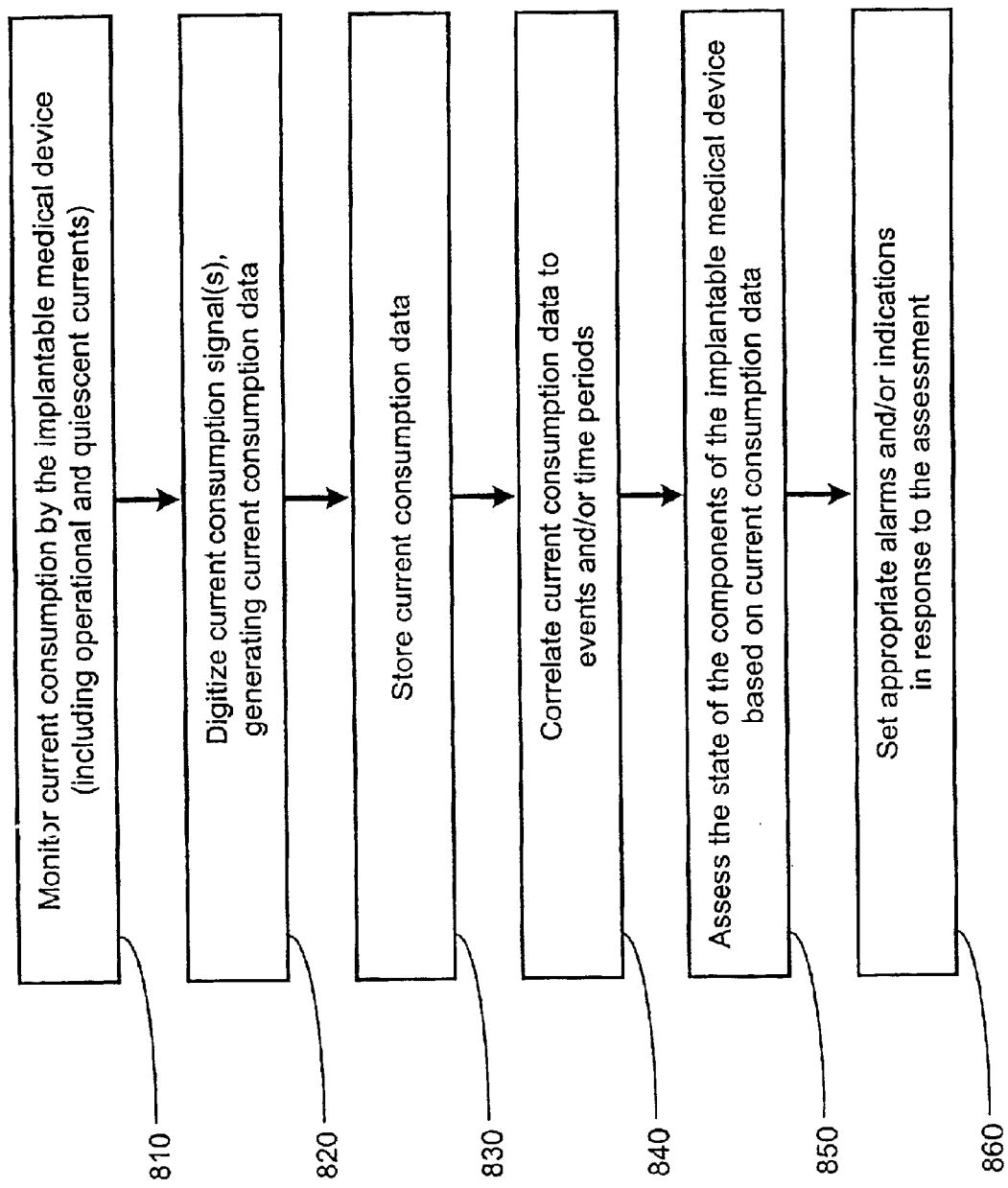
FIG. 8 illustrates a more detailed flowchart depiction of a method of performing a current monitor function in accordance with one illustrative embodiment of the present invention.

Turning now to FIG. 8, a flow chart depiction of the steps relating to the method of the present invention is illustrated. The implantable medical device 110 monitors the current consumption by the implantable medical device 110 (block 810). The monitoring of the current consumption includes monitoring operational current consumption and/or quiescent current consumption. The current monitor unit 510, in one embodiment, may generate an average current consumption of the implantable medical device 110 for a predetermined time period. The current consumption signal generated by the current monitor unit 510 is then digitized by using the ADC 520, thereby generating digital current consumption data (block 820). Digitizing the current consumption signal provides for the ability to store and/or transmit and process the current consumption data.

The implantable medical device 110 then stores the digitized current consumption signal into the memory unit 430 (block 830). The access device 240 may acquire data from the memory unit 430 for analysis of the current consumption data. Furthermore, at predetermined intervals, the processor 410 may retrieve the current consumption data from the memory unit 430 in order to perform analysis.

In one embodiment, the implantable medical device 110 correlates data relating to the current consumption of the implantable medical device 110 to events and/or time periods (block 840). For example, certain current-consumption indications may be correlated to particular events experienced by the implantable medical device 110, such as delivery of therapy, which involves charging up a capacitor for discharge. Furthermore, the data relating to the current consumption may be correlated to idle moments or quiescent moments experienced by the implantable medical device 110. Additionally, data relating to the current consumption may be correlated to particular time periods for analysis, which can provide an indication of current consumption for a certain time period, such as current consumption during delivery of therapy and/or current consumption during time periods where the implantable medical device 110 experiences quiescence.

Furthermore, an unusual current leak in the implantable medical device 110 may be detected. Using the analysis described above, a useful lifetime of the implantable medical device 110 may be calculated, in light of a faulty component and/or current leaks. Furthermore, based upon a determination that the current consumption data indicates a faulty crystal oscillator, a conclusion may be made that the hermetic seal enclosing the casing of the implantable medical device 110 may be compromised.

Based upon the correlation of the current consumption data, the implantable medical device 110 may access the state of the components of the implantable medical device 110 based upon the current consumption data (block 850). In one embodiment, the quiescent current consumption is analyzed to determine whether one or more components in the implantable medical device 110 (e.g., capacitors, inductors, resistors, transistors, crystal oscillators, etc.) may be malfunctioning. For example, a determination may be made that a particular capacitor is experiencing an inordinate amount of current leakage during a charge up or quiescent period of time. Additionally, indications of malfunction of one or more crystal oscillators that generate clock signals for the operation of the electronics in the implantable medical device 110 may be made based upon the current consumption data.

A number of symptoms and/or problems may be assessed by the analysis of the current consumption data, particularly analysis of quiescent current consumption data. Based upon the assessment, appropriate alarms and/or signals may be generated to alert the implantable medical device 110 and/or an operator who may have access to information from the implantable medical device 110 via the access device 240 (block 860). Conclusions relating to the health of the implantable medical device 110, such as the lifetime of the implantable medical device 110, or the batteries placed in the implantable medical device 110 may be made by the assessment of the current consumption data. The correlation assessment and analysis of the current consumption data may be performed by the implantable medical device 110 or, in an alternative embodiment, by a device external to the implantable medical device 110. By using the analysis of the current consumption data, a host of performance conclusions and condition of components in the implantable medical device 110 indications may be made such that improvements in the operation of the implantable medical device 110 may be performed. For example, in response to a defect being assessed based on the current consumption data, appropriate actions, such as alternate therapies may be selected, or circuits corresponding to the components of the implantable mechanical device assessed defective may be turned off to preserve battery life or to insure patient safety based on assessment of the faulty components or components. The principles described in the present disclosure can be implemented into a variety of electrical circuitry in addition to implantable medical devices 110.

The above detailed description is an illustrative example of an embodiment in accordance with the present invention, of the implementation of the implantable medical device 110 described above. It should be appreciated that other implementations and/or embodiments can be employed within the spirit of the present invention. The teachings of the present invention can be utilized for a variety of systems relating to electrical circuitry, including circuitry that utilize stored charge.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is set forth in the claims below.

What is claimed:

1. A method of evaluating component performance in an implantable medical device, comprising the steps of:
    generating a current consumption signal relating to current consumption in an implantable medical device;
    processing the current consumption signal;
    assessing a defect of a component in the implantable medical device in response to the processing of the current consumption signal; and
    switching from s first power source to a second power source based upon the processing of the current consumption signal.

2. The method described in claim 1, wherein the step of generating a current consumption signal further comprises generating a current consumption signal relating to a quiescent current related to the implantable medical device.

3. The method described in claim 1, wherein the step of generating a current consumption signal further comprises generating a current consumption signal relating to an operating current related to the implantable medical device.

4. The method described in claim 1, wherein the step of processing the current consumption signal further comprises converting the current consumption signal into a digital format to generate a current consumption data.

5. The method described in claim 4, wherein the step of processing the current consumption signal further comprises storing the current consumption data.

6. The method described in claim 1, wherein the step of processing the current consumption signal further comprises calculating an average current consumption by the implantable medical device for a predetermined time period.

7. The method described in claim 1, wherein the step of processing the current consumption signal further comprises determining whether there is an unusual current leak based upon the current consumption signal.

8. The method described in claim 7, wherein the step of assessing a defect of a component in the implantable medical device further comprises identifying a probable component in the implantable medical device corresponding to the unusual current leak.

9. The method described in claim 8, wherein the step of identifying a probable component further comprises identifying at least one of a capacitor, inductor, resistor, transistor, and a crystal oscillator that may malfunction.

10. The method described in claim 1, wherein the step of assessing a defect of a component further comprises determining whether a leak in a hermetic seal associated with the implantable medical device exists based upon the processing of the current consumption signal.

11. The method described in claim 1, further comprising the step of altering operation of the implantable medical device in response to the step of assessing a defect of a component of the implantable medical device.

12. The method described in claim 11, wherein the step of altering operation of the implantable medial device includes one of selecting alternate therapies, generating an alert signal, and turning off circuits corresponding to the assessed component.

13. A method of evaluating component performance in an implantable medical device, comprising the steps of:
    generating a current consumption signal relating to current consumption in the implantable medical device, the generated current consumption signal including at least one of a current consumption signal relating to a quiescent current corresponding to the device and a current consumption signal relating to an operating current corresponding to the device;
    determining whether there is a current leak based upon the current consumption signal; and
    identifying a component in the device corresponding to the determined current leak,
        wherein the step of determining further comprises determining whether a leak in a hermetic seal associated with the device exists based upon the current consumption signal.

14. The method described in claim 13, further comprising the step of altering operation of the implantable medical device in response to the step of assessing a defect of a component of the implantable medical device.

15. The method described in claim 14, wherein the step of altering operation of the implantable medial device includes one of selecting alternate therapies, generating an alert signal, and turning off circuits corresponding to the assessed component.

16. An implantable medical device, comprising:
    a processor;
    a control logic unit operatively coupled to the processor, the control logic unit generating at least one control signal in response to a command from the processor;
    a memory unit, operatively coupled to the control logic unit, storing and providing data to the processor via the control logic unit; and
    a power control unit, operatively coupled to the control logic unit, determining whether a component associated with the implantable medical device has malfunctioned,
        wherein the power control unit further comprises;
        a first power source and a second power source;
        a current monitor unit monitoring current consumption of the implantable medical device and generating a current consumption signal in response to the current consumption;
        an analog-to-digital converter (ADC), operatively coupled to the current monitor unit, converting the current consumption signal to a digital current consumption data; and
        power control circuitry, operatively coupled to the ADC, switching a power supply from the first power source to the second power source based upon the current consumption data.

17. The implantable medical device of claim 16, wherein the current monitor unit includes a current monitor circuit generating a current signal indicative of current consumption of the implantable medical device.

18. The implantable medical device of claim 16, wherein the processor generates a current consumption signal relating to current consumption in the device and assesses component defects in response to the current consumption signal.

19. A computer readable program storage device encoded with instructions that, when executed by a computer, performs steps, comprising:

generating a current consumption signal relating to current consumption in a implantable medical device;

processing the current consumption signal;

assessing component defects in the implantable medical device in response to the processing of the current consumption signal; and switching from a first power source to a second power based upon the processing of the current consumption signal.

20. The computer readable program storage device of claim 19, wherein the step of generating a current consumption signal comprises generating a current consumption signal relating to a quiescent current related to the implantable medical device.

21. The computer readable program storage device of claim 19, wherein the step of generating a current consumption signal comprises generating a current consumption signal relating to an operating current related to the implantable medical device.

22. The computer readable program storage device of claim 19, wherein the step of processing the current consumption signal comprises converting the current consumption signal into a digital format to generate current consumption data.

23. The computer readable program storage device of claim 22, wherein the step of processing the current consumption signal includes storing the current consumption data.

24. The computer readable program storage device of claim 19, wherein the step of processing the current consumption signal comprises calculating an average current consumption of the implantable medical device for a predetermined time period.

25. The computer readable program storage device of claim 19, wherein the step of processing the current consumption signal comprises determining whether there is a current leak based upon the current consumption signal.

26. The computer readable program storage device of claim 25, wherein the step of assessing component defect comprises identifying a probable component in the implantable medical device causing a current leak.

27. The computer readable program storage device of claim 26, wherein the step of identifying a probable component comprises identifying at least one of a capacitor, an inductor, a resistor, a transistor, and a crystal oscillator.

28. The computer readable program storage device of claim 19, wherein the step of assessing component defects comprises determining whether a leak in a hermetic seal associated with the implantable medical device exists based upon the processing of the current consumption signal.

* * * * *